(12) United States Patent
Yu et al.

(10) Patent No.: US 10,881,331 B2
(45) Date of Patent: Jan. 5, 2021

(54) RESPIRATORY MONITORING APPARATUS, METHOD AND DEVICE

(71) Applicant: Shenzhen Mindray Bio-Medical Electronics Co., Ltd., Shenzhen (CN)

(72) Inventors: Wenhan Yu, Shenzhen (CN); Hui Yu, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 695 days.

(21) Appl. No.: 15/601,885

(22) Filed: May 22, 2017

(65) Prior Publication Data

US 2017/0281058 A1 Oct. 5, 2017

Related U.S. Application Data

(63) Continuation-in-part of application No. PCT/CN2014/091904, filed on Nov. 21, 2014.

(51) Int. Cl.
| | | |
|---|---|---|
| *A61B 5/113* | (2006.01) | |
| *A61B 5/11* | (2006.01) | |
| *A61B 5/00* | (2006.01) | |
| *A61B 5/08* | (2006.01) | |

(52) U.S. Cl.
CPC .............. *A61B 5/1135* (2013.01); *A61B 5/08* (2013.01); *A61B 5/0803* (2013.01); *A61B 5/1121* (2013.01); *A61B 5/6823* (2013.01); *A61B 5/7214* (2013.01); *A61B 5/742* (2013.01); *A61B 5/7275* (2013.01); *A61B 2562/0219* (2013.01); *A61B 2562/04* (2013.01)

(58) Field of Classification Search
None
See application file for complete search history.

(56) References Cited

U.S. PATENT DOCUMENTS

| | | | |
|---|---|---|---|
| 6,522,266 B1 * | 2/2003 | Soehren | A61B 5/7264 |
| | | | 340/988 |
| 6,997,882 B1 | 2/2006 | Parker et al. | |
| 2009/0036790 A1 | 2/2009 | Landesberg et al. | |
| 2011/0021928 A1 | 1/2011 | Giovangrandi et al. | |
| 2011/0054272 A1 * | 3/2011 | Derchak | A61B 5/00 |
| 2012/0302900 A1 * | 11/2012 | Yin | A61B 5/0205 |
| | | | 600/484 |
| 2013/0172725 A1 | 7/2013 | Wu | |
| 2013/0172769 A1 | 7/2013 | Arvind et al. | |

FOREIGN PATENT DOCUMENTS

| | | |
|---|---|---|
| CN | 102946802 A | 2/2013 |
| CN | 103025240 A | 4/2013 |
| CN | 103292766 A | 9/2013 |

* cited by examiner

*Primary Examiner* — Jacqueline Cheng
*Assistant Examiner* — Jairo H Portillo
(74) *Attorney, Agent, or Firm* — Kory D. Christensen

(57) ABSTRACT

A respiratory monitoring apparatus comprises at least one motion sensor and a processing device. The at least one motion sensor senses an angular motion of a measured part capable of indicating a respiratory motion, and outputs an angular velocity vector of the measured part; the processing device, connected to the motion sensor, extracts a respiratory angular velocity from the angular velocity vector, and acquires a respiratory wave according to the respiratory angular velocity.

12 Claims, 2 Drawing Sheets

RESPIRATORY MONITORING APPARATUS, METHOD AND DEVICE

CROSS-REFERENCE TO RELATED APPLICATIONS

This application is a continuation-in-part of PCT Application No. PCT/CN2014/091904, filed Nov. 21, 2014, for "Respiratory Monitoring Apparatus, Method and Device," which is incorporated herein by reference.

TECHNICAL FIELD

The present disclosure relates to respiratory monitoring, and in particular, to apparatuses, devices, and methods for respiratory monitoring.

SUMMARY

According to a first aspect, the present disclosure provides a respiratory monitoring apparatus that may include: at least one motion sensor for at least sensing an angular motion of a measured part capable of indicating a respiratory motion, and outputting an angular velocity vector of the measured part; and a processing device, connected to the motion sensor, for extracting a respiratory angular velocity from the angular velocity vector, and acquiring a respiratory wave according to the respiratory angular velocity.

According to a second aspect, the present disclosure provides a respiratory monitoring method that may include: using at least one motion sensor to sense an angular motion of a measured part capable of indicating respiratory motion, and output an angular velocity vector of the measured part; and extracting a respiratory angular velocity from the angular velocity vector, and acquiring a respiratory wave according to the respiratory angular velocity.

According to a third aspect, the present disclosure provides a respiratory monitoring device that may include: a receiving device for receiving the angular velocity vector of a measured part on a measured object outputted by a motion sensor, wherein the angular velocity vector is outputted after the motion sensor senses an angular motion of the measured part capable of indicating respiratory motion; and a calculating device for extracting a respiratory angular velocity from the angular velocity vector, and acquiring a respiratory wave according to the respiratory angular velocity.

On the basis that the measured part has an angular velocity capable of indicating respiratory motion, the respiratory monitoring apparatus, method and device provided by the present disclosure acquire the angular velocity via the motion sensor, output the angular velocity vector of the measured part, extract the respiratory angular velocity from the angular velocity vector, and acquire the respiratory wave according to the respiratory angular velocity.

DETAILED DESCRIPTION

Several strategies for monitoring respiratory motion of the human body have been proposed.

Air-Flow Scheme

A respiratory wave can be detected by using a sensor provided at a face mask after the face mask is put on the face of a measured object (e.g., patient). The sensor is used for sensing air flow generated when the measured object breathes. The drawback of the air-flow scheme is that it is necessary to place the face mask on the face of the measured object, inconveniencing the daily life of the measured object.

Piezoelectric Scheme

The respiratory wave can be detected by using a piezoelectric sensor after the piezoelectric sensor is bound to the chest of the measured object. The piezoelectric sensor senses change of the pressure applied thereto due to contraction and expansion of the thorax when the measured object breathes. The drawback of the piezoelectric scheme is that it is necessary to lace the piezoelectric sensor fixedly to the body of the measured object, making the measured object uncomfortable to some degree.

Acceleration Scheme

The respiratory wave can be detected by using two acceleration sensors placed at the front and back of the measured object respectively in the scheme. The acceleration sensors sense change of acceleration due to contraction and expansion of the thorax when the measured object breathes. The drawback of the acceleration scheme is that it is sensitive to movement of the measured object, resulting in poor measuring accuracy.

Various technical aspects will be further described by the following detailed description of embodiments with the accompanying drawings.

Figure 1:
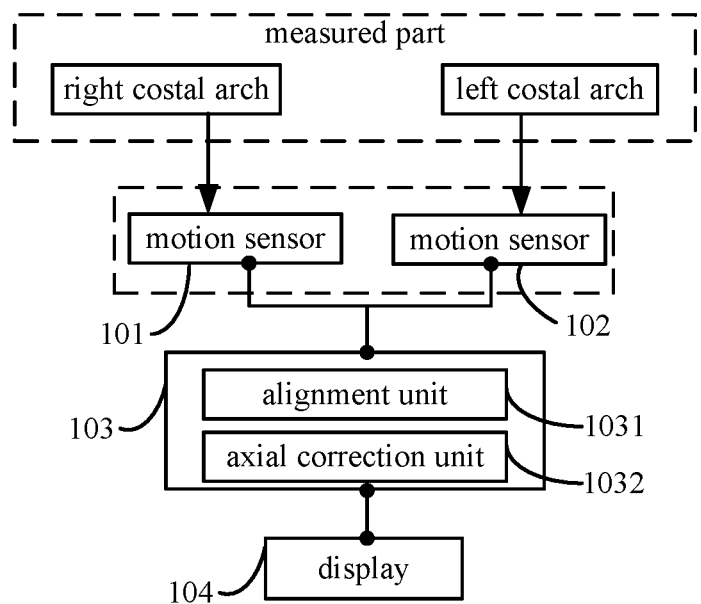
FIG. 1 is a schematic block diagram of a respiratory monitoring apparatus In one embodiment of the present disclosure.

Referring to FIG. 1, the present disclosure provides a respiratory monitoring apparatus, which includes motion sensors 101, 102 and a processing device 103.

The motion sensors 101, 102 may at least be used to sense angular motion of the measured part capable of indicting a respiratory motion, and to output an angular velocity vector of a measured part.

The processing device 103 connected to the motion sensors 101, 102 may be used to extract a respiratory angular velocity from the angular velocity vector and acquire a respiratory wave based on the respiratory angular velocity.

The respiratory monitoring apparatus may further include a display 104 connected to the processing device 103 for displaying the respiratory wave obtained by the processing device 103 in a specific embodiment.

In one embodiment, the motion sensors may be six-degree-of-freedom inertial sensors each assembled by a triaxial angular velocity sensor and a triaxial acceleration sensor for outputting the angular velocity vector, a gravity acceleration vector and a motion acceleration vector of the measured part respectively. In other embodiments, the acceleration sensor may not be required when there is no need to align sensitive axes of the motion sensors with corresponding given direction respectively or axially correct the motion sensors.

In one embodiment, the motion sensors may be triaxial angular velocity sensors; while in other embodiments, the angular velocity sensors with fewer axes, such as single-axis angular velocity sensors, could be used when there is an additional restriction, for example, defining fixed directions of sensitive axes of the angular velocity sensors, or only monitoring respiration when the measured object is at rest. In other examples, three single-axis angular velocity sensors, every two of which is placed vertically, could be used to act as a triaxial angular velocity sensor; or three single-axis acceleration sensors, every two of which placed vertically, could also be used to act as a triaxial acceleration sensor.

In some embodiments, it may be preferable to use two motion sensors; while in other embodiments, it may be possible to use only one angular velocity sensor under an additional restriction, for example, only monitoring respiration when the measured object is at rest.

Figure 2:
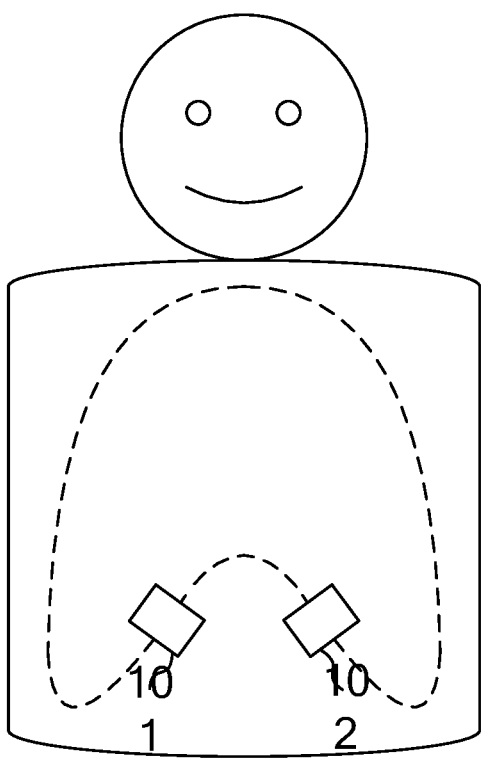
FIG. 2 is a diagram schematically showing a placement between two motion sensors in a respiratory monitoring apparatus In one embodiment of the present disclosure.

As shown in FIG. 2, the motion sensors 101, 102 are fixed at a left costal arch and a right costal arch of the measured object respectively for measuring the angular motion at both left and right costal arches. The costal arches are bone tissue formed by the 8-10th pairs of ribs, which are not directly connected with sternum but connected by costal cartilage and upper ribs. The angular motion of the measured part capable of indicating respiratory motion comes up at the costal arches when the measured object breathes; thus selecting the region of the costal arches as the measured part.

The costal arches are suitable to be placed with the motion sensors at any conditions (such as different body sizes or breathing modes, etc.); and in this embodiment, the costal arches could be used as the measured part. Under an additional condition, other parts of the measured object may be selected as the measured parts for fixing the motion sensors in other embodiments, e.g., the chest of the measured object may be selected as the measured part when measuring thoracic breathing.

In the present embodiment, using two motion sensors for measurement may serve to reduce the disturbance of human motion.

Figure 3:
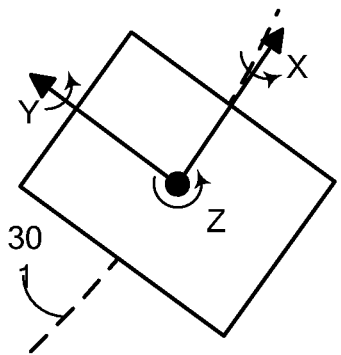
FIG. 3 is a diagram schematically showing a coordinate system of a motion sensor in a respiratory monitoring apparatus In one embodiment of the present disclosure.

FIG. 3 schematically shows a coordinate system of the motion sensor 101. A dotted line 301 is the direction of the right costal arch. Since the motion sensor 101 is a triaxial angular velocity sensor therein, the coordinate system includes x, y, z axes. When the sensitive axis (i.e., x axis) of the motion sensor is placed along a given direction, the given direction is a direction where the angular velocity vector sensed by the motion sensor is parallel to and in the same direction as its sensitive axis. The angular motion of the measured part capable of indicating respiratory motion may be come up at the costal arches when the measured object breathes. At the right costal arch, the respiratory angular velocity may be approximately parallel to and in the same direction as the x axis of the motion sensor 101, and the value of the respiratory angular velocity, which could be positive or negative, may be varied with respiration. The respiratory angular velocity could be mainly projected onto the x axis in the coordinated system of the motion sensor 101 and basically not projected onto the y and z axes. The respiratory angular velocity may have the same features at the left costal arch. However, when the value of the respiratory angular velocity at the right costal arch is positive, the value of the respiratory angular velocity at the left costal arch is negative; while the value of the respiratory angular velocity at the right costal arch is negative, the value of the respiratory angular velocity at the left costal arch is positive. That is, the projections of the respiratory angular velocities sensed respectively by the motion sensors satisfy the following relation: the projections of the respiratory velocities sensed by the x axis of the motion sensors 101, 102 are equal in value but opposite in sign.

A motion disturbance angular velocity may be sensed simultaneously by the two motion sensors when the measured object moves. The motion sensors 101, 102 may sense projections of the motion disturbance angular velocity onto the x, y, and z axes of the coordinate systems respectively. The projections sensed by the motion sensors 101, 102 respectively may meet the following correlation: a multiplication of a three-dimensional square matrix and a three-dimensional vector of the disturbance angular velocity sensed by the motion sensor 102 is equal to a three-dimensional vector of the disturbance angular velocity sensed by the motion sensor 101. The three-dimensional square matrix is the attitude transformation matrix from the coordinate system of the motion sensor 102 to the coordinate system of the motion sensor 101.

The relation between the respiratory angular velocities sensed by the two motion sensors is not equal to the relation between the disturbance angular velocities sensed by the two motion sensors. Upon this, vector equations could be built to calculate out the respiratory angular velocity. The effect of motion disturbance could be removed by separating the respiratory angular velocity from the disturbance angular velocity. The vector equations are as follows:

$$\begin{cases} \omega^a = \omega_{RA}^a + \omega_M^a \\ \omega^b = \omega_{RB}^b + \omega_M^b \\ \omega_M^a = C_b^a \omega_M^b \\ \omega_{RA}^a = -\omega_{RB}^b \end{cases} \quad (1)$$

wherein $\omega^a$ is the angular velocity vector outputted by the motion sensor 101;

$\omega^b$ is the angular velocity vector outputted by the motion sensor 102;

$\omega_{RA}{}^a$ is the respiratory angular velocity sensed by the motion sensor 101;

$\omega_{RB}{}^b$ is the respiratory angular velocity sensed by the motion sensor 102;

$\omega_M{}^a$ is the disturbance angular velocity sensed by the motion sensor 101;

$\omega_b{}^a$ is the disturbance angular velocity sensed by the motion sensor 102;

$C_b{}^a$ is the attitude transformation matrix from the coordinate system of the motion sensor 102 to the coordinate system of the motion sensor 101.

It should be noted that the angular velocity vector outputted by the motion sensor may include an actual respiratory angular velocity and the disturbance angular velocity. Therefore, the calculated result of the respiratory angular velocity may be as follows:

$$\omega_{RA}{}^a = (I_3 + C_b{}^a)^{-1}(\omega^a - C_b{}^a \omega^b) \quad (2)$$

wherein $I_3$ is a three-dimensional square matrix.

It can be seen from the formula (2) that there is no disturbance angular velocity in the calculated result of the respiratory angular velocity $\omega_{RA}{}^a$, that is, the motion disturbance has been removed. Of course, in other embodiments, the respiratory angular velocity $\omega_{RB}{}^b$ can also be calculated and removed.

It should be noted that, in some embodiments, since the measured object is in a static or small-scaled motion, the motion disturbance is small, and there may be only one motion sensor to be used, e.g., a single angular velocity sensor.

Usually, when fixing the motion sensor, it is necessary to let its x axis of the angular velocity coordinate parallel to or perpendicular to the direction of the costal arch. This is more complicated in operation. Moreover, it is also difficult to ensure the direction of the x axis by manual operation accurately points to a right direction; and if the direction of the x axis does not point to the right direction, it would result in bringing an error in the measurement.

Further, in the present embodiment, the processing device 103 may further include an axial correction device 1032 for axially correcting the motion sensors 101, 102. Axial directions for fixing the motion sensors can be random by axially correcting the motion sensors; thus ensuring ease of operation.

Since the motion sensors used in the present embodiment are triaxial acceleration sensors, the motion sensors 101, 102 also output a gravity acceleration vector of the measured part.

During axially correcting the motion sensors 101, 102 by the axial correction device 1032, the axial correction device 1032 establishes a virtual coordinate system for the motion sensors, and calculates the correlation between the coordinate system of the motion sensors and the virtual coordinate system based on the gravity acceleration vector.

When extracting the respiratory angular velocity from the angular velocity vector, the processing device 103 projects the angular velocity vector to the virtual coordinate system upon the correlation, and extracts the respiratory angular velocity from its projection value based on the calculated formula.

Ensuring that the detected angular velocity vector is only projected roughly to the x' axis of the virtual coordinate system, and the z' axis of the virtual coordinate system is parallel to or coincided with the z axis of the sensor coordinate system when building the virtual coordinate system for a certain sensor, the y' axis of the virtual coordinate system may be determined by its x', z' axes and the right-hand rule. In general, the x' axis of the virtual coordinate system, pointing to an obliquely upward direction, is substantially parallel to the direction of the costal arch where the motion sensor is located. The axial correction device 1032 then may acquire projected value of a gravity acceleration of the measured part (i.e., gravity acceleration vector) from the acceleration sensor, and calculate the attitude transformation matrix between the coordinate system and its corresponding virtual coordinate system.

In one embodiment, the attitude transformation matrix $C_{b'}^{a'}$ between two virtual coordinate systems may be calculated out according to the attitude transformation matrix $C_b^a$ between the two coordinate systems, the attitude transformation matrix $C_a^{a'}$ between the coordinate system of the motion sensor 101 and its corresponding virtual coordinate system, the attitude transformation matrix $C_b^{b'}$ between the coordinate system of the motion sensor 102 and its corresponding virtual coordinate system.

Formulas used for axially correcting the motion sensor are as follows:

$$\theta_a = \arctan\left(\frac{\overline{f_{ay}}}{\overline{f_{ax}}}\right) - \frac{\pi}{4} \quad (6)$$

$$\theta_b = \arctan\left(\frac{\overline{f_{by}}}{\overline{f_{bx}}}\right) + \frac{\pi}{4} \quad (7)$$

$$C_a^{a'} = \begin{pmatrix} \cos(\theta_a) & \sin(\theta_a) & 0 \\ -\sin(\theta_a) & \cos(\theta_a) & 0 \\ 0 & 0 & 1 \end{pmatrix} \quad (8)$$

$$C_b^{b'} = \begin{pmatrix} \cos(\theta_b) & \sin(\theta_b) & 0 \\ -\sin(\theta_b) & \cos(\theta_b) & 0 \\ 0 & 0 & 1 \end{pmatrix} \quad (9)$$

$$C_{b'}^{a'} = C_a^{a'} C_b^a (C_b^{b'})^T \quad (10)$$

$$\omega^{a'} = C_a^{a'} \omega^a \quad (11)$$

$$\omega^{b'} = C_b^{b'} \omega^b \quad (12)$$

wherein $\overline{f_{ax}}$ is a vector mean outputted at the x axis of the acceleration sensor of the motion sensor 101 in an axial correction period, and so forth;

$\theta_a$ is an axial correction angle of the angular velocity sensor of the motion sensor 101;

$\theta_b$ is an axial correction angle of the angular velocity sensor of the motion sensor 102;

$C_a^{a'}$ is an axial correction matrix of the angular velocity sensor of the motion sensor 101, that is, the attitude transformation matrix between the coordinate system of the motion sensor 101 and its corresponding virtual coordinate system;

$C_b^{b'}$ is an axial correction matrix of the angular velocity sensor of the motion sensor 102, that is, the attitude transformation matrix between the coordinate system of the motion sensor 102 and its corresponding virtual coordinate system;

$C_{b'}^{a'}$ is the attitude transformation matrix between the two virtual coordinate systems;

$\omega^a f$ is a projection of the angular velocity in the coordinate system of the motion sensor 101;

$\omega^b f$ is a projection of the angular velocity in the coordinate system of the motion sensor 102;

$\omega^{a'}$ is a projection of the angular velocity in the virtual coordinate system corresponding to the coordinate system of the motion sensor 101;

$\omega^{b'}$ is a projection of the angular velocity in the virtual coordinate system corresponding to the coordinate system of the motion sensor 102.

The formula (8) is the attitude transformation matrix between the coordinate system 101 and its corresponding virtual coordinate system; the formula (9) is the attitude transformation matrix between the coordinate system 102 and its corresponding virtual coordinate system; and the formula (10) is the attitude transformation matrix between the two virtual coordinate systems respectively corresponding to the coordinate systems 101, 102.

When the processing device 103 is obtaining the respiratory wave based on the respiratory angular velocity, the processing device 103 projects the angular velocity vector to the virtual coordinate system upon the formulas (11) and (12) respectively, extracts the respiratory angular velocity from the projection based on the formula (2), and then obtains the respiratory wave on the basis of the respiratory angular velocity. In this case, the $C_b^a$ in the formula (2) is replaced by the $C_{b'}^{a'}$ calculated upon the formula (10), the $\omega^a$ is replaced by the $\omega^{a'}$ calculated upon the formula (11), and the $\omega^b$ is replaced by the $\omega^{b'}$ calculated upon the formula (12).

To calculate the attitude transformation matrix $C_b^a$ between the two coordinate systems, the processing device 103 may also include an alignment device 1031 for aligning the motion sensors in the present embodiment. Aligning the motion sensor refers to calculate the attitude transformation matrix $C_b^a$ based on the actual placement relationship between the motion sensors 101, 102.

Since the motion sensors used in the embodiment are triaxial acceleration sensors, the motion sensors 101 and 102 also output the gravity acceleration vector and/or motion acceleration vector. The alignment device 1031 may calculate the attitude transformation matrix from the coordinate system of one motion sensor to that of the other motion sensor.

It should be note that when the measured object is at rest, the attitude transformation matrix of the coordinate system of one motion sensor to that of the other motion sensor could be calculated by sampled gravity acceleration; and while the measured object is moving, the attitude transformation matrix from the coordinate system of one motion sensor to the coordinate system of the other motion sensor could be calculated by the acceleration vector.

In a specific embodiment, the formulas used for alignment are as follows:

$$F_a = \begin{bmatrix} f_{ax}(1) & \cdots & f_{ax}(n) \\ f_{ay}(1) & \cdots & f_{ay}(n) \\ f_{az}(1) & \cdots & f_{az}(n) \end{bmatrix} \quad (3)$$

$$F_b = \begin{bmatrix} f_{bx}(1) & \cdots & f_{bx}(n) \\ f_{by}(1) & \cdots & f_{by}(n) \\ f_{bz}(1) & \cdots & f_{bz}(n) \end{bmatrix} \quad (4)$$

$$C_b^a = (F_b^T F_b)^{-1} F_b^T F_a \quad (5)$$

wherein $f_{ax}(1)$ is an x-axis output at the first sampling point by the angular velocity sensor of the motion sensor 101 during a time period for alignment, and so forth;

$f_{bx}(1)$ is an x-axis output at the first sampling point by the angular velocity sensor of the motion sensor 102 during the time period for alignment, and so forth;

$F_a$ is a matrix of vectors outputted by the acceleration sensor of the motion sensor 101 during the time period for alignment;

$F_b$ is a matrix of vectors outputted by the acceleration sensor of the motion sensor 102 during the time period for alignment;

$C_b^a$ is the attitude transformation matrix from the angular velocity coordinate system of the motion sensor 102 to the angular velocity coordinate system of the motion sensor 101.

In addition, when the sensitive axes of the motion sensors are not placed along the corresponding given direction respectively, there is also no need to align the motion sensors; and in this case, the attitude transformation matrix $C_b^a$ between the motion sensors may be replaced with a specified constant matrix. However, since it is difficult to ensure that the positions of the motion sensors 101, 102 are strictly corresponded to the corresponding attitude transformation matrix $C_b^a$, the accuracy of the measurement may be influenced.

As can be seen from the above, when the sensitive axes of the motion sensors are placed in accordance with corresponding given direction, the processing device 103 may not need to axially correct the motion sensors, the respiratory angular velocity may be extracted from the angular velocity vector by the formula (2) in which the angular velocity is that in the coordinate system, and the attitude transformation matrix is that between the two coordinate systems; and when the sensitive axes of the motion sensors are not placed along the corresponding given direction respectively, the processing device 103 may need to axially correct the motion sensors, the respiratory angular velocity may be extracted from the angular velocity vector by the formula (2) in which the angular velocity is that in the virtual coordinate system corresponding to the coordinate system, and the attitude transformation matrix is that between the two virtual coordinate systems.

In one embodiment, the respiratory monitoring apparatus may align and/or axial correct the motion sensors in a time period, e.g. from a half second to several seconds, after starting up. The alignment and/or axial correction may be carried out only one time, and can be performed simultaneously; but in different embodiments, functions of alignment and axial correction may be selectively used depending on the actual monitoring situation.

It should also be noted that, during the process of alignment and axial correction, since the gravity acceleration vector or motion acceleration vector acquired by the motion sensors are needed, the measured object may need to stand up or walk after the motion sensors are fixed on the measured part thereof; and then, after alignment and axial correction, the measured object may be in any posture, such as lying, when monitoring respiration.

Figure 4:
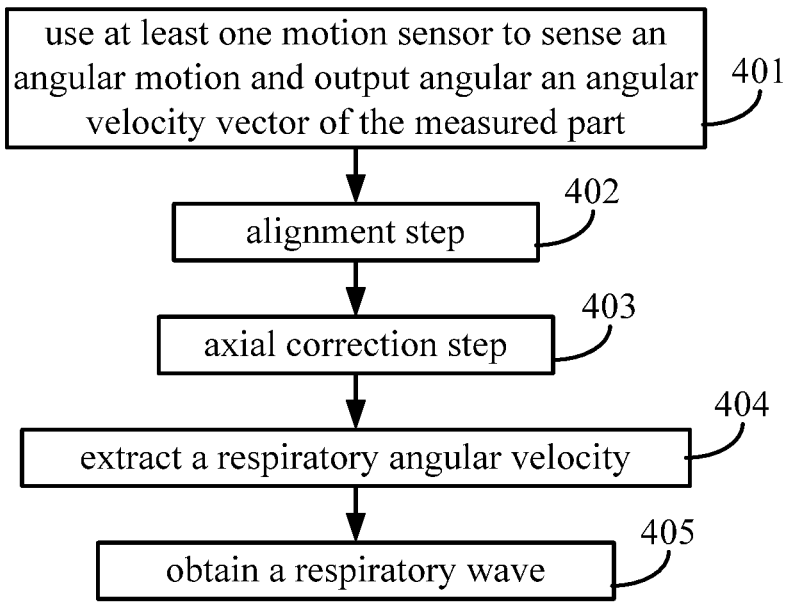
FIG. 4 is a schematic flowchart illustrating a respiratory monitoring method In one embodiment of the present disclosure.

Referring to FIG. 4, the present disclosure also includes a respiratory monitoring method, which corresponds to the above respiratory monitoring apparatus. The method may include the following steps.

Step 401: using at least one motion sensor to sense an angular motion of a measured part capable of indicating respiratory motion, and to output an angular velocity vector of the measured part. In a specific embodiment, the subsequent step of aligning and correcting the motion sensor requires the gravity acceleration vector and/or motion acceleration vector of the measured part, it may thus be preferred that the gravity acceleration vector and the motion acceleration vector of the measured part could be obtained by the motion sensor in the step 401. Furthermore, the motion sensor is a six-degree-of-freedom inertial sensor assembled by an angular velocity sensor and an acceleration sensor for obtaining the angular velocity vector, the gravity acceleration vector and the motion acceleration vector of the measured part respectively.

In one embodiment, it may be preferable to use two motion sensors for measuring angular motion at the left and right costal arches respectively. In other examples, it is possible to use only one angular velocity sensor under an additional restriction, for example, only monitoring respiration when the measured object is at rest.

Step 402 is an alignment step which may include: calculating an attitude transformation matrix from a coordinate system of one motion sensor to a coordinate system of the other motion sensor upon the gravity acceleration vector and/or motion acceleration vector.

Step 403 is an axial correction step which may include: establishing virtual coordinate systems for the two motion sensors, and calculating a correlation between the coordinate system of the motion sensors and the virtual coordinate system based on the gravity acceleration vector for each motion sensor.

Step 404: extracting a respiratory angular velocity from the obtained angular velocity vector.

Since there are two motion sensors in the embodiment, when a sensitive axis of each motion sensor is placed along the corresponding given direction, the step of extracting the respiratory angular velocity from the angular velocity vector may include: extracting the respiratory angular velocity by the following calculation formula:

$$\omega_{RA}{}^a = (I_3 + C_b{}^a)^{-1}(\omega^a - C_b{}^a \omega^b)$$

wherein $\omega^a$ is an angular velocity vector outputted by one motion sensor, $\omega^b$ is an angular velocity vector outputted by the other motion sensor, $\omega_{RA}{}^a$ is the respiratory angular velocity sensed by the one motion sensor, $C_b{}^a$ is an attitude transformation matrix from a coordinate system of the one motion sensor to a coordinate system of the other motion sensor, $I_3$ is a three-dimensional identity matrix; and with each given direction, the sensitive axis of each motion sensor is parallel to and in the same direction as its sensed angular velocity vector.

In particular, in step 404, $C_b{}^a$ is a constant matrix.

When performing the axial correction step after the sensitive axis of each motion sensor is not placed along the corresponding given direction, step 404 may include: projecting the angular velocity vector to the virtual coordinate system based on the above correlation, and then extracting the respiratory angular velocity from the projected angular velocity vector based on the above calculating formula.

When performing the alignment step, step 404 may include: calculating a corresponding attitude transformation matrix from the virtual coordinate system of one motion sensor to the virtual coordinate system of the other motion sensor based on the calculated attitude transformation matrix from the coordinate system of one motion sensor to the coordinate system of the other motion sensor, and further extracting the respiratory angular velocity from the respiratory angular velocity vector based on the above calculating formula.

Step 405: obtaining a respiratory wave from the respiratory angular velocity.

A calculating method for the respiratory wave obtained by the respiratory angular velocity is as follows.

1. Performing the integral of the respiratory angular velocity $$\Omega = \int \omega_{RA}{}^{ax} dt \quad (13)$$

wherein $\omega_{RA}{}^{ax}$ is an x-axis output of the respiratory angular velocity sensed by the motion sensor 101, and $\Omega$ is a respiratory angular position.

In other embodiments, when doing static respiratory monitoring with a single-axis or a triaxial angular velocity sensor after defining the direction of the placement, the $\omega_{RA}{}^{ax}$ in the formula (13) could be replaced by an output of the single-axis angular velocity sensor or a x-axis output of the triaxial angular velocity sensor.

In other embodiments, when doing static respiratory monitoring with a triaxial angular velocity sensor without defining the direction of the placement, the $\omega_{RA}{}^{ax}$ in the formula (13) could be replaced by a x-axis output of the virtual coordinate system after axial correcting the triaxial angular velocity sensor.

2. Filtering respiration angular position with high-pass and low-pass filters to obtain filtered respiration angular position without disturbance, i.e., the respiratory wave.

The respiratory monitoring method provided by the present embodiment works with the same principle of the above-mentioned respiratory monitoring apparatus, which will not be described here.

Figure 5:
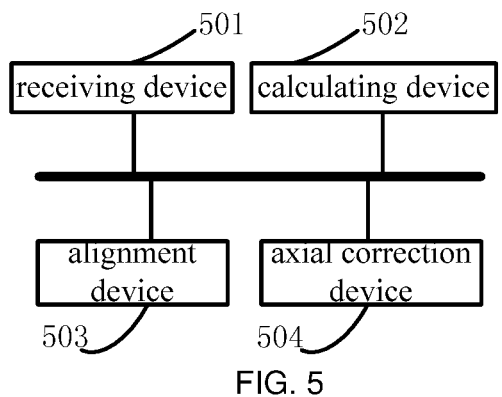
FIG. 5 is a schematic block diagram showing a respiratory monitoring device In one embodiment of the present disclosure.

Referring to FIG. 5, the present disclosure provides a respiratory monitoring device including a receiving device 501, a calculating device 502, an alignment device 503, and an axial correction device 504.

The receiving device 501 receives an angular velocity vector of a measured part of a measured object outputted by a motion sensor. The angular velocity vector is outputted after the motion sensor senses an angular motion of the measured part capable of indicating respiratory motion The calculating device 502 extracts a respiratory angular velocity from the angular velocity vector, and acquires a respiratory wave according to the respiratory angular velocity.

In one embodiment, angular velocity vectors outputted by two motion sensors are angular velocity vectors at the left and right costal arches of the measured object. When a sensitive axis of each motion sensor is placed along a corresponding given direction, the calculating device uses the following calculating formula to extract the respiratory angular velocity from the angular velocity vector:

$$\omega_{RA}{}^a = (I_3 + C_b{}^a)^{-1}(\omega^a - C_b{}^a \omega^b)$$

wherein $\omega^a$ is an angular velocity vector outputted by one motion sensor, $\omega^b$ is an angular velocity vector outputted by the other motion sensor, $\omega_{RA}{}^a$ is a respiratory angular velocity sensed by the one motion sensor, $C_b{}^a$ is an attitude transformation matrix from one motion sensor to the other motion sensor, $I_3$ is a three-dimensional identity matrix; and with each given direction, the sensitive axis of the motion sensor is parallel to, and in the same direction as, its sensed angular velocity vector sensitive axis.

In one embodiment, the receiving device 501 also receives a gravity acceleration vector outputted by the motion sensor. The respiratory monitoring device may also include an axial correction device 504 for axial correcting the motion sensors. The axial correction device 504 establishes a virtual coordinate system for each motion sensor, and based on the gravity acceleration vector, calculates a correlation between the coordinate system of the motion sensors and its virtual coordinate system.

When the sensitive axis of each motion sensor is not placed along the corresponding given direction, the calculating device 502, based on the calculated attitude transformation matrix from the coordinate system of one motion sensor to the coordinate system of the other motion sensor, calculates a corresponding attitude transformation matrix from the virtual coordinate system of one motion sensor to the virtual coordinate system of the other motion sensor, and further extracts the respiratory angular velocity from the respiratory angular velocity vector based on above calculating formula.

In one embodiment, the receiving device 501 may further receive the gravity acceleration vector and/or the motion acceleration vector outputted by the motion sensors. The respiratory monitoring device may also include an alignment device 503 for aligning the motion sensors, wherein the alignment device 503 calculates the attitude transformation matrix of one motion sensor to the other motion sensor based on the gravity acceleration vector and/or the motion acceleration vector When the sensitive axis of each motion sensor is not placed in accordance with corresponding given direction, the way the calculating device 502 extracts the respiratory angular velocity from the angular velocity vector may include: the calculating device 502 projects the angular velocity vector to the virtual coordinate system based on above correlation, and extracts the respiratory angular velocity from projected angular velocity vector based on the above calculating formula.

Specifically, when the calculating device 502 extracts the respiratory angular velocity from the respiratory angular velocity vector based on above calculating formula, $C_b^a$ is a constant matrix.

The respiratory monitoring device provided by the present embodiment works with the same principle of the above-mentioned respiratory monitoring apparatus, which will not be described here.

With the respiratory monitoring apparatus, method and device provided by the embodiments of the present disclosure, on the one hand, the respiratory wave can be obtained by the angular velocity vector obtained by the motion sensor on the basis of the appearance of the angular motion of the measured part capable of indicating respiratory motion at the junction of the measured object's chest and abdomen. On the other hand, the motion disturbance can be decreased or even reduced by fixing two motion sensors on the right and left costal arches of the measured object. At the same time, it is more convenient to fix the motion sensors with more accurate measurement due to alignment and axial correction to the motion sensor during monitoring.

Those skilled in the art can appreciate that all or part of the steps of the various methods in the above-described embodiments may be accomplished by instructing relevant hardware, such as a microprocessor, using instructions stored in a computer readable storage medium, which may include: read-only memory, random access memory, magnetic or optical disks.

Though the present disclosure has been described in detailed with aforesaid embodiments, the present disclosure is not limited by these embodiments. It can be understood by those skilled in the art that various changes can be made without departing from the spirit of the present disclosure.

The invention claimed is:

1. A respiratory monitoring apparatus, comprising:
at least one motion sensor for at least sensing an angular motion of a measured part capable of indicating respiratory motion, and outputting an angular velocity vector of the measured part;
a processing device, connected to the motion sensor, for extracting a respiratory angular velocity from the angular velocity vector, and acquiring a respiratory wave according to the respiratory angular velocity; and
a display coupled to the processing device for displaying the respiratory wave; and
wherein the at least one motion sensor comprises two motion sensors for measuring the respective angular motion at a left costal arch and a right costal arch; and
wherein, when a sensitive axis of each motion sensor is placed along a given direction, the processing device extracts the respiratory angular velocity from the angular velocity vector using the following formula:

$$\omega_{RA}^a = (I_3 + C_b^a)^{-1}(\omega^a - C_b^a \omega^b)$$

wherein $\omega^a$ is an angular velocity vector outputted by one motion sensor, $\omega^b$ is an angular velocity vector outputted by the other motion sensor, $\omega_{RA}^a$ is a respiratory angular velocity sensed by one motion sensor, $C_b^a$ is an attitude transformation matrix from a coordinate system of one motion sensor to a coordinate system of the other motion sensor, $I_3$ is a three-dimensional identity matrix; and each corresponding given direction causes the sensitive axis of a corresponding motion sensor to be parallel to and in the same direction as the angular velocity vector sensed by the corresponding motion sensor.

2. The respiratory monitoring apparatus according to claim 1, wherein each motion sensor further outputs a gravity acceleration vector of the measured part;
the processing device establishes, for each motion sensor, a virtual coordinate system for the motion sensor, and based on the gravity acceleration vector, calculates a correlation between the coordinate system of the motion sensor and the virtual coordinate system for the motion sensor; and
when the sensitive axis of each motion sensor is not placed along the corresponding given direction, in order to extract the respiratory angular velocity form the angular velocity vector, the processing device projects the angular velocity vector to the virtual coordinate system based on the correlation, and extracts the respiratory angular velocity from the projection.

3. The respiratory monitoring apparatus according to claim 1, wherein each motion sensor further outputs at least one of a gravity acceleration vector and a motion acceleration vector of the measured part;
wherein the processing device calculates the attitude transformation matrix from the coordinate system of one motion sensor to the coordinate system of the other motion sensor based on at least one of the gravity acceleration vector and the motion acceleration vector;
when the sensitive axis of each motion sensor is not placed along the corresponding given direction, based on the calculated attitude transformation matrix from the coordinate system of one motion sensor to the coordinate system of the other motion sensor, the processing device calculates an attitude transformation matrix from a virtual coordinate system of one motion sensor to a virtual coordinate system of the other motion sensor, and further extracts the respiratory angular velocity from the respiratory angular velocity vector.

4. The respiratory monitoring apparatus according to claim 1, wherein the motion sensor is an inertia sensor.

5. The respiratory monitoring apparatus according to claim 1, wherein $C_b^a$ is a constant matrix when the processing device extracts the respiratory angular velocity from the respiratory angular velocity vector.

6. A respiratory monitoring method, comprising:
using at least one motion sensor to sense an angular motion of a measured part capable of indicating respiratory motion, and output an angular velocity vector of the measured part;
extracting a respiratory angular velocity from the angular velocity vector, and acquiring a respiratory wave according to the respiratory angular velocity; and
displaying the respiratory wave;
wherein the at least one motion sensor comprises two motion sensors for measuring the respective angular motion at a left costal arch and a right costal arch; and
wherein when a sensitive axis of each motion sensor is placed long a given direction, extracting the respiratory angular velocity from the angular velocity vector using the following formula:

$$\omega_{RA}^a = (I_3 + C_b^a)^{-1}(\omega^a - C_b^a \omega^b)$$

where $\omega^a$ is an angular velocity vector outputted by one motion sensor, $\omega^b$ is an angular velocity vector outputted by the other motion sensor, $\omega_{RA}{}^a$ is a respiratory angular velocity sensed by one motion sensor, $C_b{}^a$ is an attitude transformation matrix from a coordinate system of one motion sensor to a coordinate system of the other motion sensor, $I_3$ is a three-dimensional identity matrix; and each corresponding given direction causes the sensitive axis of a corresponding motion sensor to be parallel to and in the same direction as the angular velocity vector sensed by the corresponding motion sensor.

7. The respiratory monitoring method according to claim 6, wherein the method further comprises:
using a gravity acceleration vector of the measured part outputted by each motion sensors;
axially correcting the motion sensors, wherein the step of axially correcting the motion sensors specifically comprises: for each said motion sensor, establishing a virtual coordinate system for the motion sensor and calculating a correlation between the coordinate system of the motion sensor and the virtual coordinate system for the motion sensor based on the gravity acceleration vector; and
when the sensitive axis of each motion sensor is not placed along the corresponding given direction, in order to extract the respiratory angular velocity form the angular velocity vector, projecting the angular velocity vector to the virtual coordinate system based on the correlation, and extracting the respiratory angular velocity from the projection.

8. The respiratory monitoring method according to claim 7, the method further comprises:
using at least one of a gravity acceleration vector and a motion acceleration vector of the measured part outputted by each motion sensor;
aligning the motion sensors, wherein the step of aligning the motion sensors specifically comprises: calculating the attitude transformation matrix from the coordinate system of one motion sensor to the coordinate system of the other motion sensor based on at least one of the gravity acceleration vector and the motion acceleration vector; and
when the sensitive axis of each motion sensor is not placed along the corresponding given direction, calculating a corresponding attitude transformation matrix from a virtual coordinate system of one motion sensor to a virtual coordinate system of the other motion sensor based on the calculated attitude transformation matrix from the coordinate system of one motion sensor to the coordinate system of the other motion sensor, and further extracting the respiratory angular velocity from the respiratory angular velocity vector.

9. The respiratory monitoring method according to claim 6, wherein the motion sensor is an inertial sensor.

10. A respiratory monitoring device, comprising:
a microprocessor for receiving an angular velocity vector of a measured part on a measured object outputted by a motion sensor, wherein the angular velocity vector is outputted after the motion sensor senses an angular motion of the measured part capable of indicating respiratory motion; and
wherein the microprocessor extracts a respiratory angular velocity from the angular velocity vector, and acquires a respiratory wave according to the respiratory angular velocity; and a display coupled to the microprocessor for displaying the respiratory wave;
wherein the respiratory angular velocity is extracted from angular velocity vectors outputted by two motion sensors, wherein the angular velocity vectors outputted by the two motion sensors are angular velocity vectors of the respective angular motion at a left costal arch and a right costal arch of the measured object; and
wherein a sensitive axis of each motion sensor is placed along a corresponding given direction, the microprocessor extracts the respiratory angular velocity from the angular velocity vectors using the following formula:

$$\omega_{RA}{}^a = (I_3 + C_b{}^a)^{-1}(\omega^a - C_b{}^a \omega^b)$$

wherein $\omega^a$ is an angular velocity vector outputted by one motion sensor, $\omega^b$ is an angular velocity vector outputted by the other motion sensor, $\omega_{RA}{}^a$ is a respiratory angular velocity sensed by one motion sensor, $C_b{}^a$ is an attitude transformation matrix from a coordinate system of one motion sensor to a coordinate system of the other motion sensor, $I_3$ is a three-dimensional identity matrix; and each corresponding given direction causes the sensitive axis of a corresponding motion sensor to be parallel to and in the same direction as the angular velocity vector sensed by the corresponding motion sensor.

11. The respiratory monitoring device according to claim 10, wherein the receiving device further receives a gravity acceleration vector outputted by each motion sensor;
the respiratory monitoring device further comprises an axial correction device for axially correcting the motion sensors, wherein for each motion sensor, the axial correction device establishes a virtual coordinate system for the motion sensor and calculates a correlation between the coordinate system of the motion sensor and the virtual coordinate system for the motion sensor based on the gravity acceleration vector; and
when the sensitive axis of each motion sensor is not placed along the corresponding given direction, in order to extract the respiratory angular velocity form the angular velocity vector, the microprocessor projects the angular velocity vector to the virtual coordinate system based on the correlation, and extracts the respiratory angular velocity from the projection.

12. The respiratory monitoring device according to claim 10, wherein the microprocessor receives at least one of a gravity acceleration vector and a motion acceleration vector outputted by each motion sensor and calculates the attitude transformation matrix from the coordinate system of one motion sensor to the coordinate system of the other motion sensor based on at least one of the gravity acceleration vector and the motion acceleration vector in order to align the motion sensors;
when the sensitive axis of each motion sensor is not placed along the corresponding given direction, based on the calculated attitude transformation matrix from the coordinate system of one motion sensor to the coordinate system of the other motion sensor, the microprocessor calculates a corresponding attitude transformation matrix from the virtual coordinate system of one motion sensor to the virtual coordinate system of the other motion sensor, and further extracts the respiratory angular velocity from the respiratory angular velocity vector.

* * * * *